US009809934B2

(12) United States Patent
Gourves et al.

(10) Patent No.: US 9,809,934 B2
(45) Date of Patent: Nov. 7, 2017

(54) METHOD FOR CHARACTERIZING THE SEAT OF A RAILROAD TRACK, DEVICE FOR VIEWING THE INSIDE OF A GROUND AND ASSEMBLY FOR CHARACTERIZING THE SEAT OF A RAILROAD TRACK COMPRISING SUCH A DEVICE

(71) Applicant: SOL SOLUTION, Riom (FR)

(72) Inventors: Roland Gourves, Marsat (FR); Younes Haddani, Chanonat (FR)

(73) Assignee: SOL SOLUTION, Riom (FR)

( * ) Notice: Subject to any disclaimer, the term of this patent is extended or adjusted under 35 U.S.C. 154(b) by 139 days.

(21) Appl. No.: 14/852,964

(22) Filed: Sep. 14, 2015

(65) Prior Publication Data
US 2016/0076203 A1 Mar. 17, 2016

(30) Foreign Application Priority Data

Sep. 15, 2014 (FR) ..................................... 14 58644

(51) Int. Cl.
*E02D 1/02* (2006.01)
*G01N 33/24* (2006.01)
(Continued)

(52) U.S. Cl.
CPC ............... *E01B 35/00* (2013.01); *E01B 1/00* (2013.01); *G01N 3/42* (2013.01); *G01N 3/48* (2013.01);
(Continued)

(58) Field of Classification Search
CPC ........... E02D 1/022; E02D 1/00; E02D 13/06; E02D 33/00; G01N 33/24; G01N 29/24
See application file for complete search history.

(56) References Cited

U.S. PATENT DOCUMENTS 2,796,760 A * 6/1957 Warlam ................. E02D 1/022
116/203
4,255,859 A * 3/1981 Klieman ............. G01F 23/0023
33/715
(Continued)

FOREIGN PATENT DOCUMENTS

FR 2 938 276 A1 5/2010
WO 2010/082002 A 7/2010

OTHER PUBLICATIONS

Athapaththu et al., "A new geotechnical method for natural slope exploration and analysis", Sep. 5, 2014.*
(Continued)

*Primary Examiner* — David A Rogers
(74) *Attorney, Agent, or Firm* — Young & Thompson

(57) ABSTRACT

This method makes it possible to characterize the seat of a railroad track through penetrometric and geo-endoscopic tests. It includes steps consisting of striking ram head of a light dynamic penetrometer to drive the tip of a train of rods into the seat, measuring the strength of the seat as a function of the pushing in depth of the train of rods, removing the train of rods from the seat, pushing a tube into a hole left by the train of rods, and sliding an image-recording camera inside the tube. The method includes additional automated steps consisting of measuring the position of the camera while it slides inside the tube, i.e., the dep that which the images are recorded, and couplingan analysis of the recorded images as a function of the depth with the strength measurements of the seat to characterize the different layers of the seat.

5 Claims, 4 Drawing Sheets

(51) Int. Cl.
| | |
|---|---|
| *E01B 35/00* | (2006.01) |
| *G01N 3/48* | (2006.01) |
| *E01B 1/00* | (2006.01) |
| *G01N 3/42* | (2006.01) |
| *H04N 5/225* | (2006.01) |

(52) U.S. Cl.
CPC ............. *H04N 5/225* (2013.01); *E02D 1/022* (2013.01); *H04N 2005/2255* (2013.01)

(56) References Cited

U.S. PATENT DOCUMENTS

| | | | | |
|---|---|---|---|---|
| 4,332,160 | A * | 6/1982 | Baragar | E21B 49/006 |
| | | | | 73/84 |
| 4,382,384 | A * | 5/1983 | Mitchell | G01N 3/40 |
| | | | | 73/594 |
| 4,398,414 | A * | 8/1983 | MacGregor | G01N 3/40 |
| | | | | 73/84 |
| 4,875,295 | A * | 10/1989 | Fleckenstein | G01F 23/0023 |
| | | | | 33/715 |
| 5,050,432 | A * | 9/1991 | Barritt | G01F 23/40 |
| | | | | 116/228 |
| 5,128,882 | A * | 7/1992 | Cooper | E21B 49/00 |
| | | | | 250/253 |
| 5,313,825 | A * | 5/1994 | Webster | E02D 1/022 |
| | | | | 73/81 |
| 5,533,392 | A * | 7/1996 | Kira | G01F 23/0023 |
| | | | | 33/720 |
| 5,543,972 | A * | 8/1996 | Kamewada | E21B 47/0002 |
| | | | | 175/49 |
| 5,651,285 | A * | 7/1997 | Legras | G01F 23/0023 |
| | | | | 73/290 R |
| 5,726,349 | A * | 3/1998 | Palmertree | E02D 1/022 |
| | | | | 73/84 |
| 6,115,061 | A * | 9/2000 | Lieberman | E21B 47/0002 |
| | | | | 175/49 |
| 6,427,529 | B1 * | 8/2002 | Daly | E21B 47/0003 |
| | | | | 73/152.01 |
| 6,481,110 | B1 * | 11/2002 | Butler | G01B 3/1084 |
| | | | | 33/393 |
| 6,533,502 | B2 * | 3/2003 | McVay | E02D 13/06 |
| | | | | 340/853.8 |
| 6,820,701 | B1 * | 11/2004 | Clark | E21B 47/0002 |
| | | | | 166/250.01 |
| 6,973,822 | B1 * | 12/2005 | Sawyers | E02D 1/022 |
| | | | | 73/82 |
| 7,152,467 | B2 * | 12/2006 | Slaughter | E02D 1/022 |
| | | | | 175/40 |
| 7,311,011 | B2 * | 12/2007 | Clark | E02D 1/06 |
| | | | | 73/864.74 |
| 7,938,002 | B1 * | 5/2011 | Lazos | G01F 23/0023 |
| | | | | 73/290 B |
| 8,485,024 | B2 * | 7/2013 | Kinast | G01N 3/48 |
| | | | | 73/84 |
| 8,590,711 | B2 * | 11/2013 | Vignoles | C02F 1/004 |
| | | | | 210/348 |
| 9,637,978 | B2 * | 5/2017 | Holloway | E21B 7/205 |
| 2002/0148298 | A1 * | 10/2002 | McVay | E02D 13/06 |
| | | | | 73/760 |
| 2005/0204809 | A1 * | 9/2005 | Slaughter | E02D 1/022 |
| | | | | 73/152.58 |
| 2007/0125158 | A1 * | 6/2007 | Kelleher | E02D 1/022 |
| | | | | 73/84 |
| 2007/0131453 | A1 * | 6/2007 | Yue | E02D 1/022 |
| | | | | 175/20 |
| 2010/0018296 | A1 * | 1/2010 | Zacny | E02D 1/022 |
| | | | | 73/84 |
| 2010/0024535 | A1 * | 2/2010 | Maeda | E02D 1/02 |
| | | | | 73/84 |
| 2012/0004848 | A1 * | 1/2012 | Kinast | G01N 3/48 |
| | | | | 702/2 |
| 2012/0031194 | A1 * | 2/2012 | Vignoles | C02F 1/004 |
| | | | | 73/861 |

OTHER PUBLICATIONS

Trong Vinh Duong, "On the hydro-mechanical behavior of ancient railway platforms in term of reinforcement by soil-mixing", available on https://pastel.archives-ouvertes.fr/pastel-00945680, Feb. 12, 2014.*
Roland Gourves, "The Panda Penetrometer", Laboratoire Génie Civil—Université Blaise Pascal de Clermont-Ferrand, France, available online at http://www.ticservicegroup.com.au/wp-content/uploads/2015/02/PANDA-Research-Roland-GOURVES-Laboratoire-Génie-Civil-Université-Blaise-Pascal-de-Clermont-Ferrand-France-2006.pdf, 2006.*
Paul W. Mayne, "Cone Penetration Testing State-of-Practice", Feb. 12, 2007.*
Miguel-Angel Benz-Navarrete, "Mesures dynamiques lors du battage du pentromtre", availble online at https://tel.archives-ouvertes.fr/tel-00725564, Aug. 27, 2012.*
D. D. Langton,"The PANDA—Light-weight Penetrometer for Soil Investigation and Monitoring Material Compaction", available online at http://www.ticservicegroup.com.au/wp-content/uploads/2011/11/Panda_Technical_Description_Understanding_Results_and_Correlations.pdf, 1999.*
Saussine et al., "Railway Ballast Settlement: A New Predictive Model", Proceedings of the Second International Conference on Railway Technology: Research, Development and Maintenance, 2014.*
Sol Solution, Frame Capture from online video https://www.youtube.com/watch?v=tehmjZiPeaQ, orginally published on Nov. 26, 2011.*
Haddani Younes et al.: "Geoendoscopie Application Au Diagnostic Des Reseaux Techniques Urbains Souterrains En a Service", JNGG October, Oct. 9, 2002 (Oct. 9, 2002), pp. 1-10, XP055156115, Nancy, France Extrait de l 'Internet: URL:http://www.geotech-fr.org/sites/default/files/congres/jngg/JNGG 2002 D pp Haddani.pdf [extrait le Dec. 1, 2014].
"Variable energy light weight dynamic cone penetrometer Compaction control and soil investigation System devised and developed by Sol Solution NF P 94-105 standard", Dec. 31, 2012 (Dec. 31, 2012), XP055187892, ZA des Portes de Riom Nord—BP 178-63204 RIOM cedex France Extrait de l 'Internet: URL:http://www.sol-solution.com/pdf/index/?fichier=uploads/HTMLeditor//panda 2 brochure.pdf [extrait le May 7, 2015].
DD Langton: "The Panda Light-Weight Penetrometer for Soilinvestigation and Monitoring Material Compaction", Dec. 31, 1999 (Dec. 31, 1999), XP055187897, Extrait de I ' Internet: URL:http://www.ticservicegroup.corn.au/wp-content/uploads/2011/11/Panda Technical Des cription Understanding Results and Correlations.pdf [extrait le May 7, 2015].
FR Search Report, dated May 7, 2015, from corresponding FR application.

* cited by examiner

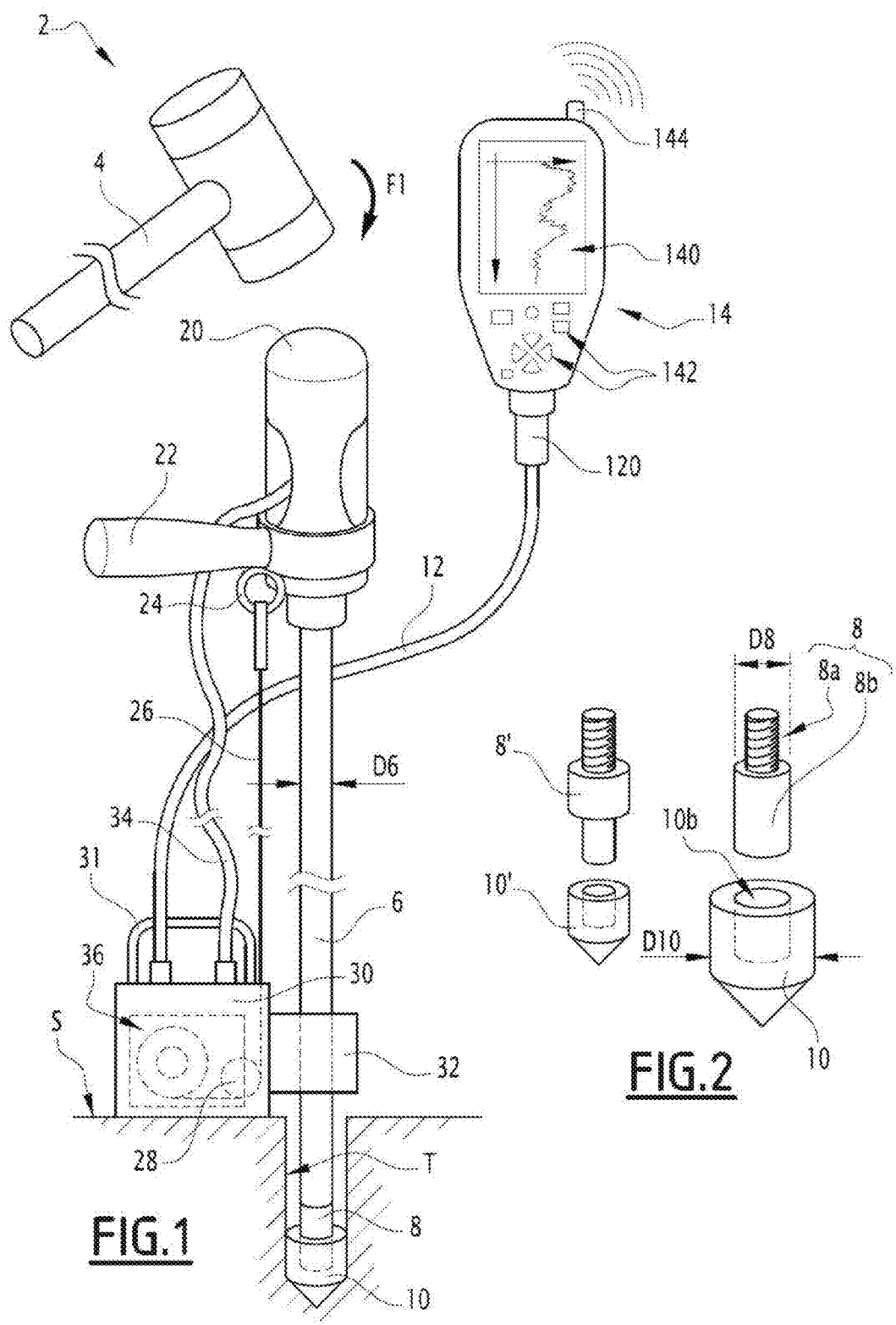

| LAYER | TYPE | NATURE | THICKNESS | COMPACTNESS | % W |
|---|---|---|---|---|---|
| A | HEALTHY BALLAST | BALLAST | 0.35 m | COMPACT | DRY |
| B | POLLUTED BALLAST | BALLAST/SANDY | 0.24 m | VERY COMPACT | WET |
| C | INTERMEDIATE COLUMN | SANDY/SILTY | 0.17 m | COMPACT | WET |
| D | PLATFORM | SILT | 0.40 m | AVERAGE | WET |

METHOD FOR CHARACTERIZING THE SEAT OF A RAILROAD TRACK, DEVICE FOR VIEWING THE INSIDE OF A GROUND AND ASSEMBLY FOR CHARACTERIZING THE SEAT OF A RAILROAD TRACK COMPRISING SUCH A DEVICE

FIELD OF THE INVENTION

The invention relates to a method for characterizing seat layers of a railroad track by coupling a penetrometric test and a geo-endoscopic test.

The invention aims to establish a geotechnical diagnosis and to obtain, as precisely as possible, parameters making it possible to characterize the nature and hydric state of the different seat layers of a railroad track in use. This in particular makes it possible to assess whether renewal or repair work is necessary on the track.

The invention also relates to a device for viewing the inside of a ground, that device commonly being called "geo-endoscope". The invention lastly relates to an assembly for characterizing a ground, comprising such a device, a light dynamic penetrometer of the Panda type (registered trademark) and a processing unit.

BACKGROUND OF THE INVENTION

Ballasted railroad tracks, developed nearly two centuries ago, are built using a set of elements designed to support the weight of the wagons. These elements include the superstructure, or line, which comprises rails, positioned on crosspieces and fasteners to fasten the rails to the crosspieces. The superstructure also comprises foundation base plates, which transmit the load supported by the rails to the ground and a ballast layer, optionally with a ballast sublayer. The ballast is a mat of crushed rocks, which ensures the uniform transmission to the platform of the stresses caused by the passage of railway vehicles. The ballast also makes it possible to stabilize the crosspieces and damp the mechanical and acoustic vibrations related to the passage of a train, which participates in the comfort of travelers onboard the trains. The ballast is further provided to drain rainwater so as to limit freezing problems on the tracks. The infrastructure is also distinguished, which is made up of a platform.

In practice, the elements of the track are designed to transmit the weight of the trains to the platform. The superstructure normally makes it possible to decrease the stress exerted on the platform by a factor of approximately 20,000 relative to that exerted at the points of contact between the wheels and the rail. This in particular makes it possible to prevent the platform from being deformed by the ballast.

The speed, the weight of the trains and the density of the traffic have increased considerably with the technological progress in recent years, which creates accelerated wear of the track components, in particular the ballast. The ballast must therefore be better maintained so that other components of the track are not damaged. Thus, the track repair operations, as well as the discontinuous and differential subsidence, are more frequent, which causes a considerable increase in maintenance costs and, in some cases, early renewal. Furthermore, it is considered that the maintenance of the ballast and the geometry of the track represent approximately half of the overall maintenance cost for railroad tracks, which is in particular due to the fact that the work is done during the night.

To withstand loads, components of the superstructure have evolved. Pre-stressed concrete crosspieces are now used, since they have a lifetime three times longer than that of wooden crosspieces. Heavier rail profiles and resilient fasteners have been developed to withstand the significant traffic. Sub-rail and sub-crosspiece base plates have been integrated into the line to damp vibrations. Geo-textiles and bituminous sublayers are applied to the base of the platform to guarantee the drainage and distribution of the loads.

However, there has been no progress regarding the protection of the ballast. To cope with the growing stresses, minimum thickness and hardness values have been imposed for the ballast. However, the latter remains the fastest-deteriorating element in a railroad track. This deterioration is accelerated by stresses due to traffic, but also by those due to maintenance work, such as packing, which have become more frequent.

The deterioration of the ballast is reflected in an attrition of the particles, i.e., a change in the grain size, as well as the rising of the ground, which is in particular caused by dynamic stresses created on the track by the passage of the trains. Two layers then appear, commonly referred to as "polluted ballast layer" and "intermediate" layer. The "polluted ballast" layer, which is located between the intermediate layer and the ballast layer, is formed by ballast as well as fines in particular coming from the attrition of the ballast. The "intermediate layer" is created by interpenetration of the layers of support ground with optional layers of material, such as broken stones, gravel, sand, or clinker, which result from the construction of the line or maintenance operations. This layer is fairly heterogeneous and contains, inter alia, more fines of the support ground and more particle fines than the ballast. The creation of these two layers within a track section poses mechanical and hydraulic stability problems, such as poor drainage, breaking of the grains of the "healthy" ballast layer, packing of the track, or deformation of the platform.

In order to cope with the deterioration of the tracks, a vast track renewal program has been launched in France. The problem that arises is to efficiently and cost-effectively establish a diagnosis of the railroad track condition, in particular aiming to detect the "polluted ballast" and "intermediate" layers. In light of the length of the tracks, the means for characterizing the ground must make it possible to monitor the large number of possible points along a track reliably, inexpensively and quickly. These means include the coring train, which makes it possible to withdraw samples of the track section. The thicknesses of the different layers of the ground are measured manually using a measuring stick or a meter stick and are transcribed manually on a worksite sheet. This monitoring technique is not the most appropriate, since only one coring train exists on the National Railway Network and the cost of this type of intervention is high. Indeed, four people, including a driver at a higher hourly rate, are generally necessary to perform the drilling. Furthermore, the coring is generally done between the two rails, whereas the most sensitive zone is below the crosspieces. This technique further lacks precision in measuring the thicknesses of the layers, since there is a risk of shifting during the raising of the core bit, especially for sandy materials. Lastly, this technique does not make it possible to measure the resistance of the ground.

A more elaborate technique consists of using a light dynamic penetrometer of the Panda type, which is a product marketed by the company SOL SOLUTION, and a geo-endoscopic test. The principle consists of measuring the strength of the ground as a function of the depth by pushing a train of rods of the penetrometer into the ground. The rods are next removed to make way for slotted tubes, in which an endoscope slides. A video is then recorded for the monitored point and is saved on a digital recorder. The interpretation of the thicknesses of the layers of ground is done manually using a meter stick, looking at the changes in nature of the soils on the screen of the geo-endoscope or the recorder. The results are next transcribed on a worksite sheet. The technician lastly performs a cross-analysis with the results obtained with the Panda penetrometer to make a diagnosis.

Although interesting, this monitoring technique is relatively time-consuming due to the manual transcription of the data, and there is no automatic and continuous measurement regarding the depth at which the images and video of the geo-endoscope are recorded. The diagnosis of the ground state is based in part on the technician's interpretation, which may lead to errors.

A similar monitoring technique is described in WO-A-2010/082002 and aims to characterize the different layers of a filtering medium, or filter, forming a water purification system. This filter comprises an upper part essentially formed by gravel, an intermediate filtration part formed by washed-out sand, and a lower part that is also gravel-based. The penetrometer test provides information on the compactness of the different layers of the filtering medium, while the endoscopic test makes it possible to verify the clogging and saturation states of the filtering medium. An automatic image analysis is done after the endoscopic test to characterize the different layers of the filtering medium, but no mention is made of an automatic measurement of the depth at which the images are taken. This measurement in fact appears to be useless in this case, since the geo-endoscopic test does not seek to determine the depth of the different layers of the filtering medium.

SUMMARY OF THE INVENTION

The invention more particularly aims to resolve these drawbacks by proposing a method for characterizing the seat of a railroad track making it possible to offset the technical and practical difficulties of implementing drilling using the current means.

To that end, the invention relates to a method for characterizing the seat of a railroad track through penetrometric and geo-endoscopic tests, the method comprising the following steps:
  a) striking a ram head of a light dynamic penetrometer to insert the tip of a train of rods into the seat,
  b) measuring the resistance of the seat as a function of the insertion depth of the train of rods,
  c) removing the train of rods from the seat,
  d) pushing a tube into a hole left by the train of rods, and
  e) sliding an image-recording camera inside the tube.

This method also comprises the following additional automated steps:
  f) continuously measuring the position of the camera while it slides inside the tube, i.e., the depth at which the images are recorded, and
  g) coupling an analysis of the recorded images as a function of the depth with the strength measurements of the ground to characterize the different layers of the seat.

Owing to the invention, systematic errors in the measurement acquisition are avoided, since the depth at which the images are taken by the camera is measured automatically. Furthermore, the performance and exploitation time of the drilling operations is shortened, since the data obtained for the geo-endoscopic and penetrometric tests are automatically coupled and analyzed.

According to advantageous but optional aspects of the invention, one method for characterizing the seat of a railroad track may include one or more of the following features, considered in any technically allowable combination:
  The method comprises an additional step consisting of geo-locating the position at which steps a) to f) are carried out.
  Step c) is carried out by leaving the tip of the train of rods at the bottom of the hole.
  The analysis of the images recorded by the camera as a function of the depth, during step g), is done from the variation of different parameters relative to the recorded images.
  Step g) includes two automated sub-steps consisting of:
    i. automatically determining significant depth values, from which the various parameters relative to the recorded images and the resistance of the seat vary considerably, and
    ii. performing a statistical analysis, for example an average, of the significant depth values to estimate the depth of the layers of the seat.
  Step g) includes another automated sub-step consisting of:
    iii) analyzing the values of the different parameters relative to the images recorded over the depth of the different layers to determine the hydric state thereof.

The invention also relates to a device for viewing the inside of a ground, comprising:
  an endoscopic camera for recording images,
  a sliding tube for the camera, which is suitable for being pushed into a hole formed in the ground.

This device further comprises:
  means for automatically and continuously measuring the position of the camera while it slides inside the tube, i.e., the depth at which the images are recorded.

According to advantageous but optional aspects of the invention, such a device can incorporate one or the other of the following features, considered in any technically allowable combination:
  The measuring means comprise a rotating coder, while the camera is suspended at the end of a wire that is wound around a moving wheel coupled to the rotating coder.
  The device is provided with a geolocation antenna.

The invention also relates to an assembly for characterizing the seat of a railroad track, comprising a light dynamic penetrometer, which includes:
  a ram head,
  a train of rods, equipped with a tip for penetrating the seat, and
  means for measuring the strength of the seat as a function of the depth.

This assembly further comprises:
  a device for viewing the inside of a ground as previously described, and
  a processing unit, configured to couple the images, recorded by the device, with strength measurements of the seat, provided by the measuring means of the penetrometer, to characterize the different layers of the seat.

BRIEF DESCRIPTION OF THE DRAWINGS

The invention and other advantages thereof will appear more clearly in light of the following description of one embodiment of a method for characterizing the seat of a railroad track according to its principle, provided solely as an example and done in reference to the drawings, in which:

FIG. 1 is a perspective view of a light dynamic penetrometer used during the implementation of a method for characterizing the seat of a railroad track according to the invention, FIG. 2 shows an exploded perspective view of a tip holder and a tip belonging to a train of rods of the dynamic penetrometer of FIG. 1 and an alternative showing a tip holder and a tip with different diameters.

DETAILED DESCRIPTION OF THE INVENTION

Figure 3:
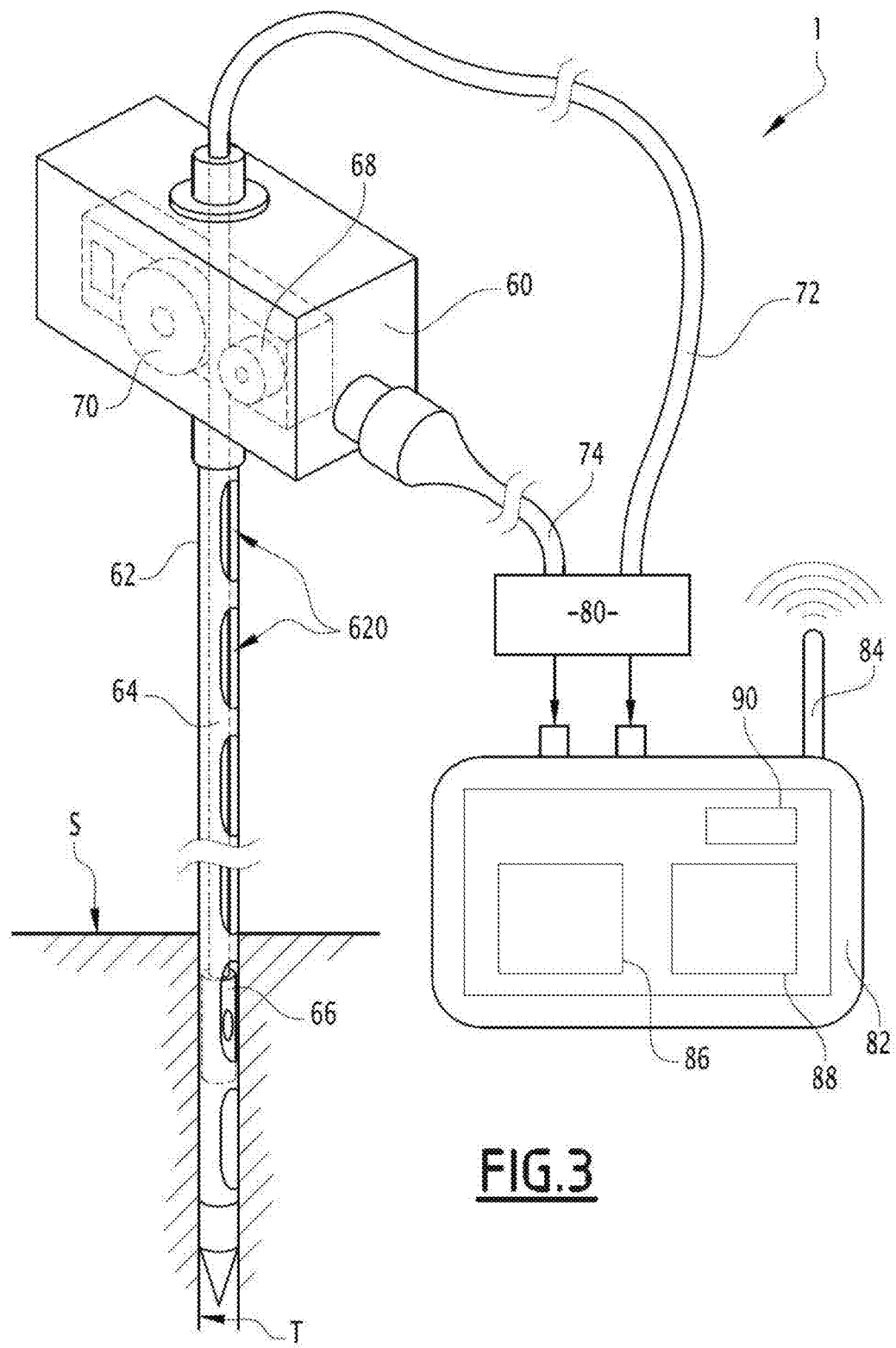
FIG. 3 is a perspective view of a device for viewing the inside of a railroad track ground according to the invention, which is also used to implement the method for characterizing the seat according to the invention.

FIG. 1 shows a light dynamic penetrometer 2 of the Panda type (registered trademark). This penetrometer 2 has a mass of less than 20 kg, such that it is easy for an operator to transport. This penetrometer 2 is also relatively compact, which facilitates interventions with restricted access. It can also be folded up quickly in case of emergency.

The dynamic penetrometer 2 extends globally along an axis Z2 which, during a test, is vertical. It includes a ram head 20 in its upper part suitable for receiving a hammer strike 4 to push a train of rods 6 into the ground. The penetrometer 2 also comprises a handle 22 to keep the train of rods 6 straight during the hammer strike. The train of rods 6 extends straight along the axis Z2 and comprises one or more cylindrical rods assembled to one another. Each rod of the train of rods 6 has a diameter D6, for example of approximately 14 mm. A tip holder 8 is screwed to a lower end of the train of rods 6. As its name indicates, the tip holder 8 is suitable for being assembled with a conical tip 10 penetrating a ground S. Here, the ground S represents the seat of a railroad track, i.e., it comprises all of the seat layers of a railroad track.

As better shown in FIG. 2, the tip holder 8 comprises a threaded upper part 8a, which makes it possible to screw it to the lower end of the train of rods 6. The tip holder 8 also comprises a lower cylinder 8b with diameter D8. In practice, the diameter D8 is the same as the diameter D6 of the rod(s) of the train of rods 6.

The conical tip 10 comprises a cylindrical upper part and a conical lower part. This tip 10 overhangs, i.e., it has a section at the base of the cone that is wider than that of the tip holder 8. In practice, the maximum diameter of the tip 10 is approximately 22 mm. This conical tip 10 comprises a cylindrical housing 10b for receiving the lower cylinder 8b of the tip holder 8. The diameter D8 of the cylinder is substantially equal to the diameter of the cylindrical housing arranged in the tip 10.

As an alternative shown in FIG. 2, a conical tip 10' that does not have an overhanging section may also be used. That conical tip 10' is provided to be assembled with a tip holder 8' with the same diameter. It discharges less soil when it is raised, but does not dig into the soil as easily as the tip 10.

The small section of one or the other of the conical tips 10 and 10' makes it possible to reduce the difficulty of the drilling and avoid closing of the drill hole during removal of the train of rods 6 from the ground.

Furthermore, the conical tip 10 or 10' is not fastened on the tip holder 8 or 8', i.e., when the train of rods 6 is removed, the conical tip 10 or 10' remains at the bottom of the drill hole. This makes it possible to prevent the tip 10 from scraping against the walls of a hole, or drill hole, T during the removal and thus prevents the hole T from being plugged up again. This is even more important when the drilled ground is of the sandy type.

The penetrometer 2 also comprises a housing 30, provided with a handle 31. This housing 30 is suitable for being placed on the ground during a test. The housing 30 comprises a portion 32 for guiding the train of rods 6 in its penetration movement in the ground S. This guiding portion 32 is crossed through by the train of rods 6 such that it cannot go askew when the ram head 20 is struck by the hammer 4.

The penetrometer 2 also comprises means for measuring the pushing in of the train of rods 6 into the ground S. These means comprise a stretched wire 26, which is attached, on the one hand, on a loop 24 rigidly connected to a moving part of the penetrometer 2, in the case at hand the ram head 20 in the example of FIG. 1, and on the other hand, to a wheel 28 contained in the housing 30. The wire 26 is kept stretched by means (not shown), such as a spring acting on the wheel. When the ram head 20 receives a hammer strike, as shown by arrow F1 in FIG. 1, the train of rods 6 and the ram head 20 become pushed into the ground S and the wire 26 relaxes. The latter is then stretched again, which causes the wheel 28 to rotate, around which the wire 26 becomes wound. The amplitude of rotation of the wheel 28 is measured by a computer 36, which is capable of deducing the depth therefrom at which the train of rods 6 has been pushed into the ground S. The computer 36 for example includes a rotating coder.

Furthermore, the housing 30 is connected to the ram head 20 via a cable 34. This cable 34 makes it possible to collect, from a force sensor, not shown, housed in the ram head 20, the ram force applied on the latter by the operator. This measurement is next sent to the computer 36. Thus, this force sensor forms, with the means for measuring the pushing in of the train of rods 6 into the ground S, means for measuring the strength of the ground as a function of the depth.

A cable 12 comprises a first end attached to the housing 30 and a second end 120 connected to a reader 14, such as a portable digital device of the "Personal Digital Assistant" type. This reader 14 comprises a screen 140 allowing the operator to view the strength of the ground as a function of the depth. It also comprises control buttons 142 and a geolocation antenna 144.

Furthermore, in FIG. 1, the train of rods 6, the cable 34, the wire 26 and the handle of the hammer 4 are cut lengthwise for better viewing.

FIG. 3 shows a device 1 for viewing the inside of a ground S. This device 1 is commonly called geo-endoscope and comprises a tube 62, suitable for being pushed vertically into a hole T arranged in the ground. The tube 62 comprises several windows 620 distributed over the entire height of the tube. These windows 620 allow a camera 66 to view the inside of the ground. In an alternative that is not shown, it is possible to consider a tube that is slotted over the entire height thereof, i.e., which does not extend over 360° in terms of section, which would allow the camera to view the images of the ground through the slot formed in the tube. The camera 66 is suspended at the end of a wire 64 and is slid manually or in a controlled manner inside the tube 62. That camera 66 is provided with lighting means (not shown), which are necessary to record images. In the example, the camera 66 is suitable for recording both images and a video sequence.

The device 1 comprises means for the automatic and continuous measurement of the position of the camera 66 while it slides inside the tube 62, i.e., the depth at which the images are recorded. These measuring means include a housing 60, which is secured to the tube 62 and which is positioned at an upper end thereof. The housing 60 is provided with an opening (not shown) for the insertion of the camera 66. It contains a wheel 68 around which the wire 64 is wound, at the end of which the camera 66 is fastened. One end of the wire 64 is therefore attached to the wheel 68. This wheel 68 is coupled to a rotating coder 70 to measure the amplitude of rotation of the wheel 68 and to deduce the movement of the camera 66 in the ground S therefrom. More specifically, as an example, the rotating coder 70 may comprise a disc rotated by the movement of the wheel 68, for example using a belt. This disc is provided with magnets, which trigger a counter when they pass in front of the sensor, for example of the Hall effect type, since they generate a magnetic field. In practice, the rotating coder 70 is an electronic coder, but it could also be an optical coder.

The device 1 comprises two cables 72 and 74, which each come from the housing 60 and which are connected to an adapter 80. The cable 72 sends the adapter 80 the images and/or videos taken by the camera 66, while the cable 74 sends the adapter 80 the measurement of the depth done by the rotating coder 70. The adapter 80 makes it possible to convert the signals sent by the camera 66 and the rotating coder 70 into a format usable by a portable digital device 82, of the "Personal Digital Assistant" type, to which it sends the information. This device 82 comprises a display interface having a dial 86 to view the video taken by the camera 66 directly and a dial 88 for the last images recorded by the camera 66. It also comprises a rectangle 90 for displaying the depth at which the camera 66 is located and a geolocation antenna 84.

In FIG. 3, the cables 72 and 74 and the tube 62 are shown partially lengthwise for better viewing.

Figure 4:
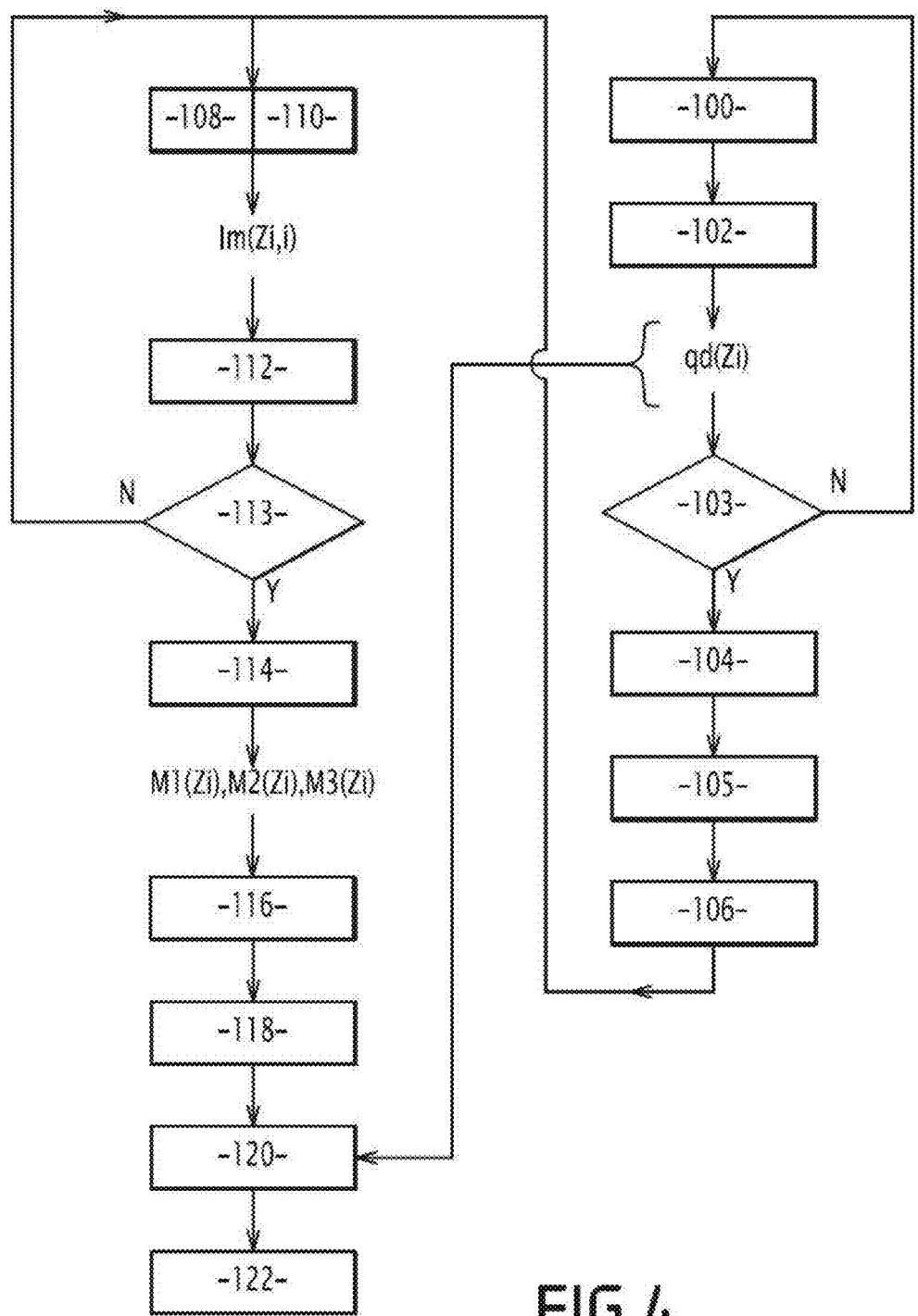
FIG. 4 is a diagram showing the different steps for carrying out the method for characterizing the seat of a railroad track according to the invention.

A method for characterizing a ground by coupling a penetrometer test and a geo-endoscopic test is described above. This method is described in reference to FIG. 4.

This method begins with a penetrometer test, which is geo-located by means of the antenna 144. During this test, the operator positions the train of rods 6 at the vertical in contact with the ground S in the selected location. The operator next takes the hammer 4 and strikes, during a step 100, the ram head 20 of the penetrometer 2 to push the tip 10 of the train of rods 6 into the ground S. The train of rods 6 then creates a hole T in the ground S.

Next, during a step 102, the variation of the strength of the ground qd(Zi) as a function of the depth Zi is determined from the measurement of the ram force exerted by the operator and the measurement of the depth Zi. It is then appropriate to determine whether the penetrometer test is complete, which is shown by a step 103 in FIG. 4. In fact, as a function of the compactness of the ground, it is possible that the operator has not struck the ram head 20 hard enough and must start the test again and strike harder to drive the train of rods 6 further into the ground S. This is shown by the loop returning to step 100.

However, if the penetrometric test is complete, i.e., if the required depth has been reached, the penetrometer 2 is capable of providing the operator with a penetrogram, which displays on the interface 140 of the reader 14. This penetrogram consists of displaying the strength of the ground, for example in MPa, as a function of the depth Zi, for example in meters. Furthermore, a first data set comprising the series of strength values qd(Zi) for each depth value Zi as well as the GPS coordinates of the test location is stored in memory during a step 104. This first data set can be stored on any appropriate support means, such as a card or key. This support means is next removed from the penetrometer 2 by an operator and connected to a processing unit (not shown), such as a worksite or office computer. This makes it possible to transfer the first data set to the processing unit. Alternatively, the first data set can be transferred from the penetrometer 2 to the processing unit directly via a wired connection or using a wireless connection.

Once the test is complete, the train of rods 6 is removed from the ground during a step 105 and the geo-endoscopic test begins. This geo-endoscopic test is geo-located, since the portable digital device 82 comprises a geolocation antenna 84. A first step 106 of this test consists of pushing the tube 62 of the geo-endoscope 1 into the hole, or drill hole, T left by the train of rods 6. Next, the camera 66 recording images is slid inside the tube 62 during a step 108.

In parallel, the position of the camera 66 inside the tube 62 is measured automatically during a step 110. In this way, it is possible to know the depth at which each image recorded by the camera 66 is recorded while the latter slides inside the tube 62. Unlike the measuring techniques known from the prior art, where the position of the camera 66 was measured manually using a meter stick pushed into the tube when the operator appeared to see a change in the type of ground on the screen of the geo-endoscope, the position of the camera 66 is measured electronically, i.e., automatically and continuously, using the rotating coder 70. This makes it possible to reduce the measurement errors regarding the camera position and facilitates the interpretation of the results. Here, the continuous measurement means that the measuring points are separated by a negligible value for the application in question. In practice, the coder 70 makes it possible to measure the position of the camera 66 every 1 mm.

During the geo-endoscopic test, a second data set comprising the images Im(Zi, i) recorded by the camera 66, the depth Zi at which each image has been recorded and the GPS coordinates of the test location is stored in memory during a step 112. This second data set can be stored on any appropriate support means, such as a card or key. This support means can next be removed from the device 1 by an operator and connected to the processing unit. This makes it possible to transfer the second data set to the processing unit. Alternatively, the second data set can be transferred from the device 1 to the processing unit directly over a wired connection or using a wireless connection.

Subsequently, the method comprises a step 113 for determining whether the geo-endoscopic test is complete, i.e., whether the camera 66 has reached the bottom of the hole T. If not, the geo-endoscopic test continues until the camera 66 reaches the bottom of the hole T, as shown by the return loop toward steps 108 and 110. However, if the test is complete, the operator can transfer the second data set in the processing unit.

This processing unit performs an analysis 114 of the images recorded by the camera 66 as a function of the depth at which they were taken. This analysis consists of setting a variation of various parameters relative to the images recorded by the camera 66 as a function of the Zi. More specifically, the processing of images done by the processing unit is based on the analysis of three parameters M1(Zi), M2(Zi) and M3(Zi), which are characteristics of the images recorded by the camera 66 as a function of the depth. In practice, these three parameters M1(Zi), M2(Zi) and M3(Zi) reflect variations of different values related to the images, such as the contrast, brightness, etc. The three parameters M1(Zi), M2(Zi) and M3(Zi) are stored in memory within the geo-endoscope during a step 116. In an alternative that is not shown, a higher or lower number of parameters may be used for the analysis.

Figures 5, 6:
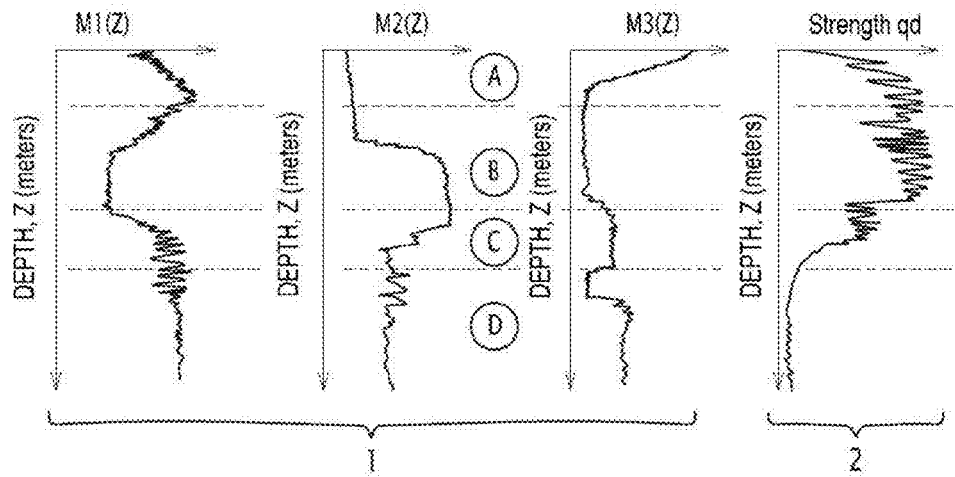
FIG. 5 shows an example of a penetrogram and an example of three graphs illustrating the variation of parameters relative to the images recorded using the device of FIG. 3, as a function of the depth in the ground.
FIG. 6 is an example of a results table obtained by implementing the ground characterization method according to the invention.

The processing unit can display, during a step 118, graphs for viewing the three parameters M1(Zi), M2(Zi) and M3(Zi) as a function of the depth Zi. One example of such graphs is shown in FIG. 5. In that figure, various zones A, B, C and D can be seen that come from variations observed in the different graphs. As shown by the two brackets in FIG. 5, graphs of the three parameters M1(Zi), M2(Zi) and M3(Zi) are obtained using the geo-endoscope 1, while the penetrogram is obtained using the light dynamic penetrometer 2.

The fact that the penetrometric and geo-endoscopic tests are both geo-localized makes it possible, in the event several tests are conducted in different locations spaced apart from one another, for the processing unit to couple, or associate, each first data set with the corresponding second data set. This further makes it possible to inventory all of the test locations on a map.

By coupling between the results from the geo-endoscopic test and those from the penetrometric test, the processing unit compiles the first data set and the second data set and automatically distinguishes, using an algorithm implemented during step 120, the changes in ground type, i.e., the different zones A, B, C and D. More specifically, step 120 comprises a first sub-step consisting of automatically determining significant depth values (Zi), from which the different parameters M1(Zi), M2(Zi) and M3(Zi) relative to the recorded images and the strength of the ground qd(Zi) vary considerably. Next, step 120 comprises a second sub-step consisting of performing a statistical analysis, for example an average, of the significant depth values to estimate the thickness of the layers of the ground S as precisely as possible.

The coupling step 120 includes a third automated sub-step consisting of analyzing the values of the different parameters M1(Zi), M2(Zi) and M3(Zi) relative to the images recorded over the thickness of the different layers to determine the hydric state of the latter.

Upon finishing step 120, an estimated table is provided of the nature, compactness, thickness and hydric state of these different layers making up the drilled ground. One example of such a table is shown in FIG. 6. This table is displayed by the processing unit during step 122.

As previously mentioned, steps 110, 112, 114 and 120 are automated, i.e., they are performed automatically by the processing unit, the penetrometer 2 or the geo-endoscope 1, without human intervention.

In the example, the hydric state of the different layers of the ground S is determined using the geo-endoscopic test, i.e., from the variation of the parameters M1(Zi), M2(Zi) and M3(Zi) as a function of the depth. The nature of the different layers of the ground is determined from the compactness and hydric state values. For example, the first layer of the drilled ground has a high compactness and a low water content, the processing unit then deducing that this is probably a ballast layer. Conversely, since the last layer is very wet and has an average compactness, the processing unit categorizes it as a silt layer.

This automatic processing of the images from the geo-endoscopic test and the automatic coupling with the ground strength data obtained using the penetrometer 2 makes it possible to obtain a rapid characterization of the ground state and its composition. The penetrometer 2, the device 1 and the processing unit form an assembly for characterizing a ground. For safety reasons, it may be provided that one skilled in the art validates the results from the processing unit, for example by comparing it with the video recorded by the geo-endoscope 1.

The technical features of the alternatives and embodiments considered above may be combined to create new embodiments of the invention.

The invention claimed is:

1. A method for characterizing a seat of a railroad track through penetrometric and geo-endoscopic tests, the method comprising the following steps:
   a) striking a ram head of a light dynamic penetrometer to insert a tip of a train of rods into the seat,
   b) measuring the resistance of the seat as a function of an insertion depth of the train of rods,
   c) removing the train of rods from the seat,
   d) pushing a tube into a hole left by the train of rods, and
   e) sliding an image-recording camera inside the tube, and the following additional automated steps:
   f) continuously measuring the position of the camera while the camera slides inside the tube, i.e., the depth at which the images are recorded, and
   g) coupling an analysis of the recorded images as a function of the depth with the strength measurements of the seat to characterize different layers of the seat,
      wherein the analysis of the images recorded by the camera as a function of the depth, during step g), is done from the variation of different parameters relative to the recorded images and wherein step g) includes two automated sub-steps consisting of:
      i. automatically determining significant depth values, from which the various parameters relative to the recorded images and the resistance of the seat vary considerably, and
      ii. performing a statistical analysis of the significant depth values to estimate the depth of the layers of the seat.

2. The method according to claim 1, wherein it comprises an additional step consisting of geo-locating the position at which steps a) to f) are carried out.

3. The method according to claim 1, wherein step c) is carried out by leaving the tip of the train of rods at the bottom of the hole.

4. The method according to claim 1, wherein step g) includes another automated sub-step consisting of:
   iii. analyzing the values of the different parameters relative to the images recorded over the depth of the different layers to determine the hydric state thereof.

5. An assembly for characterizing a seat of a railroad track, comprising a light dynamic penetrometer, which includes:
   a ram head,
   a train of rods, equipped with a tip for penetrating the seat,
   measuring means for measuring the strength of the seat as a function of the depth, a device for viewing the inside of a ground, comprising an endoscopic camera for recording images, a sliding tube for the camera, which is suitable for being pushed into a hole formed in the ground, and measuring means for automatically and continuously measuring the position of the endoscopic camera while the camera slides inside the sliding tube, i.e., the depth at which the images are recorded, and a processing unit, configured to couple an analysis of the images, recorded by the device, with strength measurements of the seat, provided by the measuring means of the penetrometer, to characterize different layers of the seat, wherein the analysis of the images recorded by the camera as a function of the depth is done from the variation of different parameters relative to the recorded images and wherein the processing unit is capable of:

i. automatically determining significant depth values, from which the various parameters relative to the recorded images and the resistance of the seat vary considerably, and ii. performing a statistical analysis of the significant depth values to estimate the depth of the layers of the seat.

\* \* \* \* \*